United States Patent [19]
Goel et al.

[11] Patent Number: 4,515,983
[45] Date of Patent: May 7, 1985

[54] MANUFACTURE OF PHENYL ESTERS AND PHENOL

[75] Inventors: Anil B. Goel, Worthington; Michael E. Pettiford, Dublin, both of Ohio

[73] Assignee: Ashland Oil, Inc., Ashland, Ky.

[21] Appl. No.: 509,476

[22] Filed: Jun. 30, 1983

[51] Int. Cl.$^3$ .................. C07C 27/14; C07C 39/04; C07C 69/157; C07C 69/22
[52] U.S. Cl. ............................ 560/130; 560/131; 568/801; 568/802
[58] Field of Search ............ 560/131, 130; 568/801, 568/802

[56] References Cited

U.S. PATENT DOCUMENTS

| | | | |
|---|---|---|---|
| 3,642,873 | 2/1972 | Hörnig et al. | 562/408 |
| 3,651,127 | 3/1972 | Hörnig et al. | 560/1 |
| 3,875,020 | 4/1975 | Tamura et al. | 203/43 |
| 3,959,352 | 5/1976 | Onoda et al. | 560/131 |
| 3,959,354 | 5/1976 | Onoda et al. | 560/131 |
| 4,016,200 | 4/1977 | Onoda et al. | 560/131 |
| 4,464,303 | 8/1984 | Goel | 560/131 X |
| 4,465,633 | 8/1984 | Goel et al. | 560/131 X |

FOREIGN PATENT DOCUMENTS

68/1415 3/1968 South Africa.
1185373 3/1970 United Kingdom.

Primary Examiner—Natalie Trousof
Assistant Examiner—Patricia M. Scott
Attorney, Agent, or Firm—John F. Jones

[57] ABSTRACT

A process for the preparation of phenyl esters and phenol in which a feed mixture of benzene, molecular oxygen, a lower carboxylic acid and optionally water is passed over a catalyst composed of a palladium carboxylate, an antimony carboxylate and a chromium carboxylate is described.

9 Claims, No Drawings

MANUFACTURE OF PHENYL ESTERS AND PHENOL

CROSS-REFERENCE TO RELATED PATENT APPLICATIONS

This Application is an improvement over the invention described in copending U.S. patent application of Anil B. Goel and Peter E. Throckmorton, Ser. No. 441,360, Filed Nov. 15, 1982.

This invention relates to the manufacture of phenyl esters and phenol from benzene and more particularly pertains to the manufacture of phenyl esters and phenol by the vapor phase reaction of benzene, molecular oxygen and a carboxylic acid in the presence of a catalyst composed of compounds of palladium, antimony and chromium.

The preparation of phenyl esters and phenol by the vapor phase reaction of benzene, oxygen and a carboxylic acid in the presence of a compound of palladium and optionally a carbonate or acylate of an alkali metal or an alkaline earth metal has been described in U.S. Pat. No. 3,651,127. Other vapor phase reactions of this type in which a catalyst containing palladium has been used appear in British Pat. No. 1,185,373; French Pat. No. 1,563,257; and in U.S. Pat. Nos. 3,642,873; 3,959,354 and 3,959,352. In general, the prior art processes produce phenyl esters and phenol in relatively low yields, and often biphenyl is also produced in the process.

We have discovered a process for preparing phenyl esters and phenol without the usual formation of biphenyl which comprises reacting in the vapor phase of mixture of benzene, molecular oxygen and a carboxylic acid in the presence of a catalyst composed of a chromium carboxylate, a palladium carboxylate and an antimony carboxylate. The catalyst of our invention is preferably supported on a carrier. As carrier or support material for the catalyst of our process, one can use alumina, silica, silica-alumina, carbon, diatomaceous earth, clay, bauxite, magnesia, zeolites, etc. Most preferred as carrier for our catalyst is alumina. The molar ratios of Pd/Sb/Cr in our catalyst can be in the range of 1/50/50 to 1/0.01/0.01, the more preferred range is from 1/20/20 to 1/0.1/0.1 The amount (by weight) of palladium which can be on the carrier can vary within the range of 0.05 to 10% and preferably in the range of 0.1 to about 5%.

Carboxylic acids which can be used in our process are those having from 2 to 6 carbon atoms. Because our process is a vapor phase reaction, the lower carboxylic acids are preferred and for convenience acetic acid is most preferred.

The amount of oxygen used in our process can vary and is preferably outside the explosive range and usually is from 1–50 mole percent of the total gaseous feed. Preferably molecular oxygen is from 2 to 20 mole% of the gaseous feed. The molecular oxygen used in our process can be pure oxygen or it can be diluted with an inert gas such as nitrogen, argon, etc.

Although the process of our invention is usually carried out at about atmospheric pressure, it can be performed at pressures greater than atmospheric.

The temperature of reaction of our process when carried out at atmospheric pressure is usually at or slightly above the boiling point of the carboxylic acid being used. Although reaction temperatures in the range of from 140° C. to 350° C. are useful in our process, the preferred range is from 180° C. to 250° C.

The ratio of benzene to carboxylic acid can be selected from a broad range and is not critical. Usually at least a slight molar excess of carboxylic acid over benzene is preferred in order to insure longer catalyst life. The preferred molar ratio of benzene to carboxylic acid falls in the range of from 1:1 to 1:10. In the process of our invention only a small amount of phenol is formed and no biphenyl is formed. The addition of water to the reactants does not affect the reaction adversely and even has been found to be beneficial in some respects.

The catalyst used in our process is very durable and shows long life with little or no loss of activity when used over long periods of time.

The process of our invention contemplates the recycling of the product stream to increase the overall conversions and yield of desired products.

The catalyst of our process has significantly better activity than prior art catalysts and shows excellent selectivity to phenyl ester and phenol. In our process the formation of small amounts of phenol does not appear to cause any catalyst deactivation as does occur in many prior art processes.

The process of our invention is further illustrated in the following examples.

EXAMPLE 1

A solution of $Pd(OAc)_2$, $Sb(OAc)_2$, and $Cr(OAc)_3$ in acetic acid was prepared by dissolving 1.48 g. (6 millimols) of $Cr(OAc)_3.H_2O$, 1.79 g. (6 millimols) of $Sb(OAc)_3$ and 1.35 g. (6 millimols) of $Pd(OAc)_2$ in about 200 ml of glacial acetic acid at about 60° C. To this solution was added 92 g. of activated alumina which had been predried at 400° C. for at least 3 hours under a stream of nitrogen. The resulting mixture was allowed to stand at room temperature overnight and the volatile material was then removed from it at reduced pressure on a rotary evaporator. The catalyst thus obtained was dried at about 60° C. under reduced pressure. The resulting catalyst was found by analysis to contain 0.66% Pd, 0.75% Sb and 0.54% Cr by weight. A 37 g. sample of this catalyst was placed in a reaction tube made of Pyrex glass having an inner diameter of about 1.75 cm. A gaseous mixture of benzene (12.2 g./hour as liquid), acetic acid (28 g./hour as liquid) and oxygen (900 ml/hour as gas diluted with 90% nitrogen) was passed through the reaction tube to affect a continuous reaction at 190° C. The products formed during each hour were found to be phenyl acetate and phenol (95/5) with amounts in terms of moles of products/mole of Pd/hour in the range of 9–11. No biphenyl was detected in the product.

EXAMPLE 2

The process of Example 1 was followed except that 18 g. of the catalyst was used and half the amounts of benzene (6.1 g./hour) and acetic acid (14 g./hour) were fed. The gaseous mixture containing benzene, acetic acid, oxygen and nitrogen was passed through the catalyst at 190° C. for about 80 hours. The amounts of phenyl acetate/phenol formed per mole of Pd after the indicated times on stream are given in Table 1.

TABLE 1

| Hours on Stream | 1 | 5 | 15 | 30 | 50 | 70 |
|---|---|---|---|---|---|---|
| Moles Product/ | 6.2 | 5.3 | 6.4 | 6.3 | 6.3 | 6.2 |

TABLE 1-continued

| Hours on Stream | 1 | 5 | 15 | 30 | 50 | 70 |
|---|---|---|---|---|---|---|
| Moles of Pd | | | | | | |

EXAMPLE 3

The procedure of Example 2 was repeated except that the reaction temperature was varied from 180° C. to 240° C. The results are given in Table 2.

TABLE 2

| Reaction Temp., °C. | 180 | 190 | 200 | 220 | 240 |
|---|---|---|---|---|---|
| Moles of Product/ Mole of Pd | 4.9 | 6.3 | 6.3 | 6.2 | 3.5 |

EXAMPLE 4

This Example demonstrates the recycling of the reaction mixture over the catalyst. The procedure of Example 1 was repeated except that 18 g. of catalyst was used and the reaction mixture was recycled over the catalyst three times after the initial pass over the catalyst. The results are given in Table 3.

TABLE 3

| Pass No. | Initial Conc., % | | Final Conc., % | | Change in Concentration, % | |
|---|---|---|---|---|---|---|
| | Ester | Phenol | Ester | Phenol | Ester | Phenol |
| 1 | 0 | 0 | 1.9 | 0.1 | 1.9 | 0.1 |
| 2 | 1.9 | 0.1 | 3.8 | 0.3 | 1.9 | 0.2 |
| 3 | 3.8 | 0.3 | 5.6 | 0.5 | 1.8 | 0.2 |
| 4 | 5.6 | 0.5 | 6.8 | 0.8 | 1.2 | 0.3 |

EXAMPLE 5

A solution was prepared by dissolving 2.97 g. of $Cr(OAc)_3.H_2O$, 3.59 g. of $Sb(OAc)_3$ and 2.69 g. of $Pd(OAc)_2$ in 250 ml. of acetic acid at about 60° C. To this solution was added 129.5 g. of gamma-alumina which had been dried. The resulting mixture was allowed to stand at room temperature overnight and the volatile material was then removed from it at reduced pressure on a rotary evaporator. The catalyst was dried under an atmosphere of nitrogen at 400° C. and then reduced with 10% hydrogen in nitrogen for one hour at 400° C. The reactor was then charged with 13.5 g. of the catalyst and the acyloxylation of benzene was carried out in a manner similar to that described in Example 1 using a feed containing a molar ratio of 1:3 benzene: acetic acid which was fed to the reactor at the rate of 0.32 g./min. Analysis of the product stream showed 4% phenyl acetate and 0.1% phenol were present.

EXAMPLE 6

A paste was prepared from 37.2 g. of omega-6 zeolite with Catapal binder (15.2 g.) in 60 ml. of water containing 3 ml. of concentrated nitric acid. The resulting paste was dried at 200° C. overnight and the dried material was broken into 20–40 mesh size. Some of this support (34.8 g.) was treated with a solution of 6 millimols of each of $Pd(OAc)_2$, $Sb(OAc)_3$ and $Cr(OAc)_3$ in acetic acid. The catalyst was dried and a 10.2 g. portion was used as in Example 1 to acetoxylate benzene using a feed containing a 1:3 molar ratio of benzene: acetic acid at a rate of 0.32 g./minute. Analysis of the product stream showed that 0.45% phenol and 1.4% of phenyl acetate and no biphenyl were formed.

We claim:

1. A process for preparing phenyl esters and phenol consisting essentially of reacting in the vapor phase a feed of benzene, molecular oxygen and a carboxylic acid in the presence of a palladium carboxylate, an antimony carboxylate and a chromium carboxylate wherein the carboxylic acid and the carboxylates are the same and have from 2 to 6 carbon atoms at a temperature in the range of from 140° C. to 350° C. and at about atmospheric pressure.

2. The process of claim 1 wherein the molar ratio of palladium: antimony: chromium is from 1:50:50 to 1:0.1:0.1.

3. The process of claim 2 wherein the molecular oxygen is present in from 1–50 mole percent of the total gaseous feed.

4. The process of claim 3 wherein the mole ratio of Benzene to the carboxylic acid in the feed is in the range of from 1:1 to 1:10.

5. The process of claim 4 wherein the catalyst is on a carrier.

6. The process of claim 5 wherein the carboxylic acid is acetic acid.

7. The process of claim 6 wherein the carrier is alumina.

8. The process of claim 6 wherein the carrier is a zeolite.

9. A process for preparing phenyl esters and phenol consisting essentially of reacting in the vapor phase a feed of benzene, molecular oxygen, water and a carboxylic acid in the presence of a palladium carboxylate, an antimony carboxylate and a chromium carboxylate wherein the carboxylic acid and the carboxylates are the same and have from 2 to 6 carbon atoms at a temperature of from 140° C. to 350° C. and at about atmospheric pressure.

* * * * *